United States Patent
Zyck et al.

(10) Patent No.: US 6,663,849 B1
(45) Date of Patent: *Dec. 16, 2003

(54) ANTACID CHEWING GUM PRODUCTS COATED WITH HIGH VISCOSITY MATERIALS

(75) Inventors: Daniel J. Zyck, North Riverside, IL (US); Michael J. Greenberg, Northbrook, IL (US); David G. Barkalow, Deerfield, IL (US); Scott W. Marske, LaGrange, IL (US); Philip W. Urnezis, Lombard, IL (US); Philip Mazzone, Griffith, IN (US)

(73) Assignee: Wm. Wrigley Jr. Company, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/653,669

(22) Filed: Sep. 1, 2000

(51) Int. Cl.[7] .......................... A61K 9/68; A61K 47/00
(52) U.S. Cl. ..................... 424/48; 424/439; 424/440; 424/441
(58) Field of Search .................. 424/48, 440, 400, 424/603, 715, 441, 439

(56) References Cited

U.S. PATENT DOCUMENTS

| | | |
|---|---|---|
| 1,298,670 A | 4/1919 | Cramer |
| 1,629,461 A | 5/1927 | Berg et al. |
| 2,892,753 A | 6/1959 | Schmidt et al. |
| 2,990,328 A | 6/1961 | Lincoln |
| 3,011,949 A | 12/1961 | Bilotti |
| 3,029,189 A | 4/1962 | Hardy et al. |
| 3,047,461 A | 7/1962 | Hardy et al. |
| 3,075,884 A | 1/1963 | Bilotti et al. |
| 3,196,172 A | 7/1965 | Wright, Jr. et al. |
| 3,308,022 A | 3/1967 | Cummings et al. |
| 3,498,964 A | 3/1970 | Hayashi |
| 3,554,767 A | 1/1971 | Daum |
| 3,590,057 A | 6/1971 | Suzuki et al. |
| 3,845,217 A | 10/1974 | Ferno et al. |
| 3,877,468 A | 4/1975 | Lichtneckert et al. |
| 3,901,248 A | 8/1975 | Lichtneckert et al. |
| 3,995,064 A | 11/1976 | Ehrgott et al. |
| 4,154,814 A | 5/1979 | Hand et al. |
| 4,238,475 A | 12/1980 | Witzel et al. |
| 4,238,510 A | 12/1980 | Cherukuri et al. |
| 4,250,195 A | 2/1981 | Cherukuri et al. |
| 4,283,408 A | 8/1981 | Hirata et al. |
| 4,317,838 A * | 3/1982 | Cherukuri et al. .......... 426/291 |
| 4,374,858 A | 2/1983 | Glass et al. |
| 4,378,374 A | 3/1983 | Reggio et al. |
| 4,386,063 A | 5/1983 | Boden |

(List continued on next page.)

FOREIGN PATENT DOCUMENTS

| | | |
|---|---|---|
| DE | 43 42 568 A1 | 6/1994 |
| EP | 0 202 819 A2 | 11/1986 |
| EP | 0 217 109 A2 | 4/1987 |

(List continued on next page.)

OTHER PUBLICATIONS

Merriam Webster's Collegiate Dictionary, Syrup, p. 1197 (1998).*

(List continued on next page.)

*Primary Examiner*—Thurman K. Page
*Assistant Examiner*—Robert M. Joynes
(74) *Attorney, Agent, or Firm*—Steven P. Shurtz; Brinks Hofer Gilson & Lione

(57) ABSTRACT

A method of making antacid coated chewing gum products comprises the steps of providing chewing gum cores; providing a coating syrup comprising a bulk sweetener, calcium carbonate and a binding agent; and applying the coating syrup to the cores and drying the syrup to produce a sugarless coating on the cores. The coating on the cores produces a high viscosity in saliva when the gum is chewed, in that 4.5 grams of said coating dispersed in 30 ml of water has a Brookfield viscosity at 23° C. of at least 1.6 centipoise.

27 Claims, 1 Drawing Sheet

U.S. PATENT DOCUMENTS

| | | |
|---|---|---|
| 4,386,106 A | 5/1983 | Merritt et al. |
| 4,400,372 A | 8/1983 | Muhker et al. |
| 4,446,135 A | 5/1984 | Fountaine |
| 4,452,821 A | 6/1984 | Gergely |
| 4,459,311 A | 7/1984 | DeTora et al. |
| 4,474,749 A | 10/1984 | Kruppa |
| 4,512,968 A | 4/1985 | Komiyama et al. |
| 4,533,556 A | 8/1985 | Piccolo et al. |
| 4,555,407 A | 11/1985 | Kramer et al. |
| 4,563,345 A | 1/1986 | Arrick |
| 4,639,368 A | 1/1987 | Niazi et al. |
| 4,647,450 A | 3/1987 | Peters et al. |
| 4,711,774 A | 12/1987 | Denick, Jr. et al. |
| 4,716,033 A | 12/1987 | Denick, Jr. |
| 4,737,366 A | 4/1988 | Gergely et al. |
| 4,753,800 A | 6/1988 | Mozda |
| 4,753,805 A | 6/1988 | Cherukuri et al. |
| 4,755,389 A | 7/1988 | Jones et al. |
| 4,758,424 A | 7/1988 | Denick, Jr. et al. |
| 4,822,597 A | 4/1989 | Faust et al. |
| 4,822,816 A | 4/1989 | Markham |
| 4,828,820 A | 5/1989 | Glass et al. |
| 4,832,994 A | 5/1989 | Fey |
| 4,835,162 A | 5/1989 | Abood |
| 4,849,227 A | 7/1989 | Cho |
| 4,853,212 A | 8/1989 | Faust et al. |
| 4,867,989 A * | 9/1989 | Silva et al. ................. 424/440 |
| 4,882,152 A | 11/1989 | Yang et al. |
| 4,894,234 A | 1/1990 | Sharma et al. |
| 4,908,211 A | 3/1990 | Paz |
| 4,908,212 A | 3/1990 | Kwon et al. |
| 4,929,447 A | 5/1990 | Yang |
| 4,929,508 A | 5/1990 | Sharma et al. |
| 4,933,184 A | 6/1990 | Tsuk |
| 4,935,242 A | 6/1990 | Sharma et al. |
| 4,938,963 A | 7/1990 | Parnell |
| 4,944,949 A | 7/1990 | Story et al. |
| 4,963,369 A | 10/1990 | Song et al. |
| 4,968,511 A | 11/1990 | D'Amelia et al. |
| 4,968,716 A | 11/1990 | Markham |
| 4,971,079 A | 11/1990 | Talapin et al. |
| 4,971,787 A | 11/1990 | Cherukuri et al. |
| 4,975,270 A | 12/1990 | Kehoe |
| 4,978,537 A | 12/1990 | Song |
| 4,997,659 A | 3/1991 | Yatka et al. |
| 5,013,716 A | 5/1991 | Cherukuri et al. |
| 5,015,464 A | 5/1991 | Strobridge |
| 5,045,325 A | 9/1991 | Lesko et al. |
| 5,070,085 A | 12/1991 | Markham |
| 5,110,608 A | 5/1992 | Cherukuri |
| 5,124,156 A | 6/1992 | Shibata et al. |
| 5,126,151 A | 6/1992 | Bodor et al. |
| 5,139,787 A | 8/1992 | Broderick et al. |
| 5,139,794 A | 8/1992 | Patel et al. |
| 5,154,927 A | 10/1992 | Song et al. |
| 5,156,842 A | 10/1992 | Mulligan |
| 5,179,122 A | 1/1993 | Greene et al. |
| 5,182,099 A | 1/1993 | Jonsson et al. |
| 5,229,137 A | 7/1993 | Wolfe |
| 5,244,670 A | 9/1993 | Upson et al. |
| 5,284,657 A | 2/1994 | Lu et al. |
| 5,286,500 A | 2/1994 | Synosky et al. |
| 5,294,433 A | 3/1994 | Singer et al. |
| 5,294,449 A | 3/1994 | Greenberg |
| 5,340,566 A | 8/1994 | Curtis et al. |
| 5,378,131 A | 1/1995 | Greenberg |
| 5,380,530 A | 1/1995 | Hill |
| 5,380,535 A | 1/1995 | Geyer et al. |
| 5,397,580 A | 3/1995 | Song et al. |
| 5,410,028 A | 4/1995 | Asami et al. |
| 5,419,919 A | 5/1995 | Song et al. |
| 5,433,960 A | 7/1995 | Meyers |
| 5,445,834 A | 8/1995 | Burger et al. |
| 5,455,286 A | 10/1995 | Amidon et al. |
| 5,456,677 A | 10/1995 | Spector |
| 5,487,902 A | 1/1996 | Andersen et al. |
| 5,488,962 A | 2/1996 | Perfetti |
| 5,494,685 A | 2/1996 | Tyrpin et al. |
| 5,496,541 A | 3/1996 | Cutler |
| 5,512,306 A | 4/1996 | Carlsson et al. |
| 5,523,097 A | 6/1996 | Song et al. |
| 5,534,272 A | 7/1996 | Bernstein |
| 5,536,511 A | 7/1996 | Yatka |
| 5,543,160 A | 8/1996 | Song et al. |
| 5,554,380 A | 9/1996 | Cuca et al. |
| 5,569,477 A | 10/1996 | Nesbitt |
| 5,571,528 A | 11/1996 | Lee et al. |
| 5,571,543 A | 11/1996 | Song et al. |
| 5,576,344 A | 11/1996 | Sandler et al. |
| 5,580,590 A | 12/1996 | Hartman |
| 5,582,855 A | 12/1996 | Cherukuri et al. |
| 5,585,110 A | 12/1996 | Kalili et al. |
| 5,593,685 A | 1/1997 | Bye et al. |
| 5,601,858 A | 2/1997 | Mansukhani |
| 5,605,698 A | 2/1997 | Ueno |
| 5,607,697 A | 3/1997 | Alkire et al. |
| 5,618,517 A | 4/1997 | Miskewitz |
| 5,628,986 A | 5/1997 | Sanker et al. |
| 5,629,013 A | 5/1997 | Upson et al. |
| 5,629,026 A | 5/1997 | Davis |
| 5,629,035 A | 5/1997 | Miskewitz |
| 5,645,853 A | 7/1997 | Winston et al. |
| 5,651,987 A | 7/1997 | Fuisz |
| 5,656,652 A | 8/1997 | Davis |
| 5,665,386 A | 9/1997 | Bebet et al. |
| 5,665,406 A | 9/1997 | Reed et al. |
| 5,667,802 A | 9/1997 | Grimberg |
| 5,693,334 A | 12/1997 | Miskewitz |
| 5,698,215 A | 12/1997 | Kalili et al. |
| 5,702,687 A | 12/1997 | Miskewitz |
| 5,711,961 A | 1/1998 | Reiner et al. |
| 5,716,928 A | 2/1998 | Benet et al. |
| 5,736,175 A | 4/1998 | Cea et al. |
| 5,744,164 A | 4/1998 | Chauffard et al. |
| 5,753,255 A | 5/1998 | Chavkin et al. |
| 5,756,074 A | 5/1998 | Ascione et al. |
| 5,800,847 A | 9/1998 | Song et al. |
| 5,824,291 A | 10/1998 | Howard |
| 5,834,002 A | 11/1998 | Athanikar |
| 5,846,557 A | 12/1998 | Eisenstadt et al. |
| 5,854,267 A | 12/1998 | Berlin et al. |
| 5,858,383 A | 1/1999 | Precopio |
| 5,858,412 A | 1/1999 | Staniforth et al. |
| 5,858,413 A | 1/1999 | Jettka et al. |
| 5,858,423 A | 1/1999 | Yajima et al. |
| 5,866,179 A | 2/1999 | Testa |
| 5,877,173 A | 3/1999 | Olney et al. |
| 5,882,702 A | 3/1999 | Abdel-Malik et al. |
| 5,889,028 A | 3/1999 | Sandborn et al. |
| 5,889,029 A | 3/1999 | Rolf |
| 5,897,891 A | 4/1999 | Godfrey |
| 5,900,230 A | 5/1999 | Cutler |
| 5,912,007 A | 6/1999 | Pan et al. |
| 5,912,030 A | 6/1999 | Huziinec et al. |
| 5,916,606 A | 6/1999 | Record et al. |
| 5,922,346 A | 7/1999 | Hersh |
| 5,922,347 A | 7/1999 | Häusler et al. |
| 5,928,664 A | 7/1999 | Yang et al. |
| 5,958,380 A | 9/1999 | Winston et al. |
| 5,958,472 A | 9/1999 | Robinson et al. |
| 5,980,955 A | 11/1999 | Greenberg et al. |

| | | | |
|---|---|---|---|
| 5,989,588 A | 11/1999 | Korn et al. | |
| 6,024,988 A | 2/2000 | Ream et al. | |
| 6,066,342 A | 5/2000 | Gurol et al. | |
| 6,077,524 A | 6/2000 | Bolder et al. | |
| 6,090,412 A | 7/2000 | Hashimoto et al. | |
| 6,165,516 A | 12/2000 | Gudas et al. | |
| 6,200,604 B1 | 3/2001 | Pather et al. | |
| 6,221,402 B1 | 4/2001 | Itoh et al. | |
| 6,258,376 B1 | 7/2001 | Athanikar | |
| 6,290,985 B2 | 9/2001 | Ream et al. | |
| 6,303,159 B2 | 10/2001 | Barkalow et al. | |
| 6,322,806 B1 | 11/2001 | Ream et al. | |
| 6,350,480 B1 | 2/2002 | Urnezis et al. | |
| 6,355,265 B1 | 3/2002 | Ream et al. | |
| 2001/0036445 A1 | 11/2001 | Anthanikar | |
| 2002/0012633 A1 | 1/2002 | Gmunder et al. | |
| 2002/0022057 A1 | 2/2002 | Battery et al. | |

FOREIGN PATENT DOCUMENTS

| | | | |
|---|---|---|---|
| EP | 0 221 850 A2 | 5/1987 | |
| EP | 0 239 541 A2 | 9/1987 | |
| EP | 0 371 584 A2 | 6/1990 | |
| EP | 0 273 809 B1 | 7/1998 | |
| FR | 2 345 938 | 10/1977 | |
| FR | 2 635 441 | 2/1990 | |
| FR | 2 706 771 | 6/1993 | |
| GB | 0 934 596 | 8/1963 | |
| GB | 0 963 518 | 7/1964 | |
| GB | 1 489 832 | 10/1977 | |
| GB | 2 181 646 A | 4/1987 | |
| IT | 02173487 | 7/1997 | |
| IT | 01293655 | 3/1999 | |
| JP | 86-242561 | 10/1986 | |
| JP | 91-112450 | 5/1991 | |
| JP | 91-251533 | 11/1991 | |
| JP | 94-303911 | 11/1994 | |
| JP | 96-19370 | 1/1996 | |
| KR | 94-2868 | 4/1994 | |
| WO | WO 84/02271 | 6/1984 | |
| WO | WO 90/12511 | 11/1990 | |
| WO | WO 90/12583 | 11/1990 | |
| WO | WO 92/06680 | 4/1992 | |
| WO | WO 95/00038 | 1/1995 | |
| WO | WO 95/00039 | 1/1995 | |
| WO | WO 95/10290 | 4/1995 | |
| WO | WO 96/00070 | 1/1996 | |
| WO | WO 96/03975 | 2/1996 | |
| WO | WO 97/21424 | 6/1997 | |
| WO | WO 97/24036 | 6/1997 | |
| WO | WO 98/23165 | 6/1998 | |
| WO | WO 98/23166 | 6/1998 | |
| WO | WO 98/23167 | 6/1998 | |
| WO | WO 99/27798 | 6/1999 | |
| WO | WO 99/33352 | 7/1999 | |
| WO | WO 99/44436 | 9/1999 | |
| WO | WO 00/13523 | 3/2000 | |
| WO | WO 00/35296 A1 * | 6/2000 | A23G/3/30 |
| WO | WO 00/35296 * | 6/2000 | A23G/3/30 |
| WO | WO 00/35298 | 6/2000 | |
| WO | WO 00/38532 | 7/2000 | |
| WO | WO 02/13781 A1 | 2/2002 | |

OTHER PUBLICATIONS

Beckett, A. H. et al., "Buccal absorption of basis drugs and its application as an in vivo model of passive drug transfer through lipid membranes", *J. Pharm. Pharmac., 19 Suppl,* 1967, pp 31S–41S.

David S. Weinberg et al. "Sublingual absorption of selected opioid analgesics", *Clin. Pharmacol Ther.,* 1998, vol. 44, pp. 335–342.

U.S. patent application Ser. No. 09/681,935, filed Jun. 28, 2001.

U.S. patent application Ser. No. 09/924,914, filed Aug. 8, 2001.

U.S. patent application Ser. No. 09/955,870, filed Sep. 19, 2001.

U.S. patent application Ser. No. 09/956,445, filed Sep. 19, 2001.

U.S. patent application Ser. No. 09/990,628, filed Nov. 13, 2001.

U.S. patent application Ser. No. 09/992,122, filed Nov. 13, 2001.

U.S. patent application Ser. No. 10/024,631, filed Dec. 17, 2001.

U.S. patent application Ser. No. 10/044,113, filed Jan. 9, 2002.

Brochure for "Minerals Technologies Specialty Minerals", 1998, 19 pages.

Akitoshi et al., Abstract "Acceleration of Transdermal Absorption of Pharmaceuticals by Essential Oils and Organic Solvents," Chem. Abst., 112:125228t, 1990.

Bradford, A Rapid and Sensitive Method for the Quantification of Microgram Quantities of Protein Utilizing the Principle of Protein–Dye Binding, Analytical Biochemistry, 72:248–254 (1976).

Nielsen et al., P–Glycoprotein as Multidrug Transporter: A Critical Review of Current Multidrug Resistant Cell Lines, Chimica et Biophysica Acta., 1139:169–183 (1992).

Adams, M.W., d–Alpha Tocopheryl Polyethylene glycol 1000 Succinate (Eastman vitamin E TPGS) as an Emulsifier and Bioenhancer for Drugs and Lipophilic Compounds, 6th International Conference on Pharmaceutical Technology, Paris, Jun. 2–4, 1992.

Beckett, A. H. et al., "Buccal absorption of basic drugs and its application as an in viov model of passive drug transfer through lipid membranes", (1967) *J. Pharma. Pharmac.,* Suppl. No. 19, pp. 31S–41S.

Chang, Tammy et al., "The Effect of Water–Soluble Vitamin E on Cyclosporine Pharmacokinetics in Healthy Volunteers," Abstract in American Society to Clinical Pharmacology and Therapeutics, 57(2):163, Feb. 1995.

Hebert, Mary F. et al.; "Bioavailability of Cyclosporine with Concomitant Rifampin Administration is Markedly Less Than Predicted by Hepatic Enzyme Induction" (1992) *Clin. Pharmacol. Ther.* 52:453–457.

Kronbach, Thomas et al.; "Oxidation of Midazolam and Triazolam by Human Liver Cytochrome P450IIIA4" (1989) *Molec. Pharm.* 36:89–96.

Lalka et al.; "The Hepatic First–Pass Metabolism of Problematic Drugs" (1993) *J. Clin. Pharmacol.* 33:657–669.

Lum et al.; "Clinical Trials of Modulation of Multidrug Resistance. Pharmacokinetic and Pharmacodynamic Considerations" (1993) *Cancer* 72:3502–3514.

Muranishi, Shozo; "Absorption Enhancers" (1990) *Crit. Rev. Ther. Drug Carrier Sys.,* 7:1–33.

Somberg et al.; "The Clinical Implications of First–Pass Metabolism: Treatment Strategies for the 1990's" (1993) *J. Clin. Pharmacol.* 33:670–673.

Tam, Yun K.; "Individual Variation in First–Pass Metabolism" (1993) *Clin. Pharmacokinet.* 25:300–328.

Van Hoogdalem et al.; "Intestinal Drug Absorption Enhancement: An Overview" (1989) *Pharmacol. Ther.* 44:407–443.

Warren et al.; "Increased Accumulation of Drugs in Multidrug–Resistant Cell Induced by Liposomes" (1992) *Cancer Research* 52:3241–3245.

Watkins, Paul B.; "The Role of Cytochromes P–450 in Cyclosporine Metabolism" (1990) *J. Am. Acad. Dermacol.* 23:1301–1309.

Weinberg, David S. et al., "Sublingual absorption of selected opioid analgesics", (1988), *Clin. Pharmacol. Ther.*, Department of Neurology and Department of Pharmacology, Cornell University Medical College, pp. 335–342.

Wrighton et al.; "In Vitro Methods for Assessing Human Hepatic Drug Metabolism: Their Use in Drug Development" (1993) 25:453–484.

Wu et al.; "Use of IV and Oral Drug Levels from Cyclosporene (CsA) with Concomitant Rifampin to Differentiate Gut Absorption and Metabolism" (1993) *Pharm. Res.* 10:abstract ppdm8185.

Zamora et al.; "Physical–Chemical Properties Shared by Compounds that Modulate Multidrug Resistance in Human Loukemic Cells" (1988) *Molec. Pharmacol.* 33:454–462.

U.S. patent application Ser. No. 09/286,818, filed Apr. 6, 1999.

U.S. patent application Ser. No. 09/421,905, filed Oct. 20, 1999.

U.S. patent application Ser. No. 09/510,878, filed Feb. 23, 2000.

U.S. patent application Ser. No. 09/535,458, filed Mar. 24, 2000.

U.S. patent application Ser. No. 09/552,290, filed Apr. 19, 2000.

U.S. patent application Ser. No. 09/591,256, filed Jun. 9, 2000.

U.S. patent application Ser. No. 09/592,400, filed Jun. 13, 2000.

U.S. patent application Ser. No. 09/618,808, filed Jul. 18, 2000.

U.S. patent application Ser. No. 09/621,643, filed Jul. 21, 2000.

U.S. patent application Ser. No. 09/621,780, filed Jul. 21, 2000.

U.S. patent application Ser. No. 09/631,326, filed Aug. 3, 2000.

U.S. patent application Ser. No. 09/651,514, filed Aug. 30, 2000.

U.S. patent application Ser. No. 09/654,464, filed Sep. 1, 2000.

U.S. patent application Ser. No. 09/671,552, filed Sep. 27, 2000.

U.S. patent application Ser. No. 09/714,571, filed Nov. 16, 2000.

U.S. patent application Ser. No. 09/747,300, filed Dec. 22, 2000.

U.S. patent application Ser. No. 09/747,323, filed Dec. 22, 2000.

U.S. patent application Ser. No. 09/748,699, filed Dec. 22, 2000.

U.S. patent application Ser. No. 09/749,983, filed Dec. 27, 2000.

U.S. patent application Ser. No. 09/759,561, filed Jan. 11, 2001.

U.S. patent application Ser. No. 09/759,838, filed Jan. 11, 2001.

"Flavor Encapsulation Technologies, Flavor Unit Sweet, Product Management", H&R (undated) (published at least before Nov. 27, 1996), 25 pages.

Dr. Massimo Calanchi and Dr. Sam Ghanta, "Taste–masking of oral formulations", *Eurand International SpA, Pharmaceutical Manufacturing International*, 1996 (5 pages).

The Eurand Group, Brochure (undated) (published at least before Nov. 27, 1996), (16 pages).

Merck Index, $11^{th}$ Ed., #1635 "Caffeine" (1989), p. 248.

Merck Index, $12^{th}$ Ed., #2337 "Cimetidine" (1996), p. 383.

Merck Index, $12^{th}$ Ed., #3264 "Dimethicone" (1996), p. 544.

Merck Index, $12^{th}$ Ed., #3972 "Famotidine" (1996), p. 667.

Merck Index, $12^{th}$ Ed., #6758 "Nizatidine" (1996), p. 1143.

Merck Index, $12^{th}$ Ed., #6977 "Omeprazole" (1996), p. 1174.

Merck Index, $12^{th}$ Ed., #8272 "Rabeprazole" (1996), p. 1392.

Merck Index, $12^{th}$ Ed., #8286 "Ranitidine" (1996), p. 1395.

James G. Elliott, "Application of Antioxidant Vitamins in Foods and Beverages" *Food Technology*, (Feb., 1999), pp. 46–48.

C. Curtis Vreeland, "Nutraceuticals Fuel Confectionery Growth" *Candy R&D*, (Mar., 1999), pp. 29, 31–32, 34–35.

Kitty Broihier, R.D., Foods of Tomorrow, Milking The Nutrition Market, *Food Processing*, (Mar., 1999), pp. 41, 42 and 44.

Kitty Broihier, R.D., "Tea Time For Nutraceuticals, New Black, Green Tea Products Brew Up a Bevy Of Health Benefits", *Food Processing*; (Mar., 1999), pp. 59, 61 and 63.

Andrea Allen, Jack Neff, Lori Dahm and Mary Ellen Kuhn, "Exclusive Guide to Wellness Foods and Nutraceuticals", Food Processing (Special Supplement), (Mar., 1999).

Product package "Aspergum" distributed by Heritage Consumer Products, LLC (on sale prior to Nov. 27, 1995).

Product package "Chew & Sooth Zinc Dietary Supplement Gum" by Gumtech International, Inc. (undated) (on sale prior to Jun. 9, 2000).

Product package "Dental Care the Baking Soda Gum" distributed by Church & Dwight Co., Inc. (1998).

Product package "BreathAsure Dental Gum" distributed by Breath Asure, Inc. (1998).

Product package "Trident Advantage with Baking Soda" distributed by Warner–Lambert Co. (1998).

Product package "CHOOZ Antacid/Calcium Supplement with Calcium Carbonate" distributed by Heritage Consumer Products Co. (undated) (on sale prior to Jun. 9, 2000).

Heritage Consumer Products Co. article from the Internet "Cosmetics and Toiletries, The Heritage Story", printed Jul. 20, 2000, <http://www.cnewsusa.com/Connecticut/14997.html>, 1 page.

The United States Pharmacopeia The National Formulary—"General Information", dated Jan. 1, 1990 pp 1624–1625 and pp 1696–1697.

Gumtech article from the Internet "Customized Solutions For Customer Brands", printed Oct. 18, 2000, <http://www.gum–tech.com/cus–brands.html>, 3 pages.

Rabeprazole article from the Internet "Rabeprazole: Pharmacokinetics and Safety in the Elderly", printed Sep. 22, 2000, <http://www.mmhc.com/cg/articles/CG9905/Humphries.html>, 2 pages.

Product package for Stay Alert Caffeine Supplement Gum, distributed by Amurol Confections Company (first quarter 1998).

* cited by examiner

ANTACID CHEWING GUM PRODUCTS COATED WITH HIGH VISCOSITY MATERIALS

BACKGROUND OF THE INVENTION

The present invention relates to methods for producing coated chewing gum products. More particularly, the invention relates to producing coated chewing gum products containing an antacid which is added to the chewing gum coating such that it will have a fast initial release and an increased residence time in the gastrointestinal tract for maximum effectiveness.

Coated chewing gum products are well known. Many prior art patents disclose chewing gum products coated with sugar sweeteners or polyol sweeteners. U.S. Pat. No. 4,317,838, for example, discloses a method of applying a sugarless coating to chewing gum. The coating may include calcium carbonate as an anti-sticking agent. Synthetic sweeteners, including many different high-intensity sweeteners, are also suggested for use in the coating.

Another area of interest is the use of medicaments in chewing gum. In some instances, it is contemplated that an active medicament that is added to the chewing gum may be released readily. An active medicament may be added to the gum coating, which is a water soluble matrix, such that during the chewing period, the medicament may be released quickly, resulting in a fast release. This would allow a chewing gum coating to be a carrier for an active medicament, specifically an antacid with these fast release characteristics. For example, U.S. Pat. No. 4,867,989 discloses a chewing gum composition coated with an outer shell containing layers of a mineral compound and a coating syrup, but this patent states that the mineral compound must be added separately and not dispersed in the syrup used to make the coating.

Antacids are usually taken on an "as needed" basis to relieve gastrointestinal disturbances mostly due to dietary indiscretions. These antacids are generally insoluble inorganic salts such as calcium carbonate, magnesium carbonate, calcium hydroxide, magnesium hydroxide, or aluminum hydroxide.

These antacids readily neutralize acids in the gastrointestinal tract and are commonly available in or as antacid tablets.

Previously, antacids have been added to chewing gum and in a chewing gum coating, but some products have not been totally consumer acceptable. The large amount of active antacid needed for effectiveness does not lend itself to giving a good tasting product. Also, the presence of sugar in the antacid chewing gum or coated on the chewing gum of some products is not consumer acceptable because sugar causes dental caries.

A sugarless coated chewing gum product having an antacid in a sorbitol base coating is currently being sold under the trademark CHOOZ.® It has been found that by adding the antacid to a gum coating, the antacid is quickly released from the chewing gum into saliva and into the gastrointestinal (GI) tract. Relief from GI disturbances is quickly obtained, but does not last long. It would be desirable to have not only fast relief, but extended relief from GI disturbances. Thus, there is a need for a way to make coated chewing gum products that have an increased residence time in the GI tract, as well as being acceptable to the consumer from taste and other standpoints.

SUMMARY OF THE INVENTION

It has been found that materials can be included in a coating syrup that is used to make a chewing gum coating containing an antacid that will make a more viscous solution than previously used coating ingredients. The result is an increase in the residence time of the antacid in the gastrointestinal tract, therefore, giving extended relief. Also, it has surprisingly been found that the antacid, like calcium carbonate, can be added as a suspension to the coating syrup to thus be included in the gum coating.

In a first aspect, the invention is a method of making antacid coated chewing gum products comprising the steps of providing chewing gum cores; providing a coating syrup comprising a bulk sweetener; calcium carbonate and a binding agent; and applying the coating syrup to the cores and drying the syrup to produce a sugarless coating on the cores; wherein the coating on the cores produces a high viscosity in saliva when the gum is chewed, in that 4.5 grams of said coating dispersed in 30 ml of water has a Brookfield viscosity at 23° C. of at least 1.6 centipoise. The bulk sweetener is preferably a disaccharide polyol such as maltitol, hydrogenerated isomaltulose, or lactitol, which gives an increased viscosity of the gum coating containing the antacid. This increased viscosity allows the antacid to remain in the gastrointestinal tract for a longer period of time, giving not only fast relief, but also longer lasting relief from stomach acidity.

In a second aspect, the invention is an antacid coated chewing gum product comprising a chewing gum core and an antacid coating on the core, the coating comprising about 30% to about 73% maltitol; about 25% to about 60% precipitated calcium carbonate; and greater than 2% of a binding agent. The use of a binding agent, such as various natural gums and cellulose gums, increases the viscosity of the coating solution and, when chewed, increases the residence time of the antacid in the gastrointestinal tract. These gums include gum arabic, gum talha, guar gum, karaya gum, locust bean gum, alginate gums, xanthan gum, arabinogalactan, various cellulose derivatives, vegetable gums, gelatin and mixtures thereof, with gum arabic being preferred.

In a third aspect, the invention is a method of delivering an antacid to an individual that provides relief in the gastrointestinal tract comprising the steps of: 1) providing an antacid coated chewing gum product having a chewing gum core and an antacid coating on the core, the coating containing about 25% to about 60% calcium carbonate and a disaccharide polyol, the coating producing a Brookfield viscosity when 4.5 grams of coating are dispersed in 30 ml of water at 23° C. of at least 1.6 centipose; and 2) chewing the antacid coated chewing gum product in the mouth and swallowing the coating, the coating dispersing and dissolving to produce an increased viscosity in saliva swallowed with the coating such that the calcium carbonate has an increased residence time in the gastrointestinal tract.

Preferred embodiments of the invention include the addition of histamine $H_2$—receptor antagonists. These agents inhibit or block the secretion of gastric acid by binding to a specific histamine receptor on the par ietal (acid secreting) cell membranes located in the stomach. These agents, which may be added to the chewing gum center or to the antacid coating containing calcium carbonate, are used for extended relief of gastrointestinal disturbances and extended relief from stomach acidity. Examples of histamine $H_2$—receptor antagonists are cimetidine, ranitidine, nizatidine, and famotidine, with famotidine being preferred.

It is believed that providing the antacid in a chewing gum coating that produces an increased viscosity in the saliva when the coating is dispersed and dissolved upon chewing makes the antacid more effective. Thus, an advantage of an embodiment of the present invention is administering an antacid to an individual in a coated product that provides extended relief while still achieving the effect of fast relief.

DETAILED DESCRIPTION OF THE PREFERRED EMBODIMENTS

Figure 1:
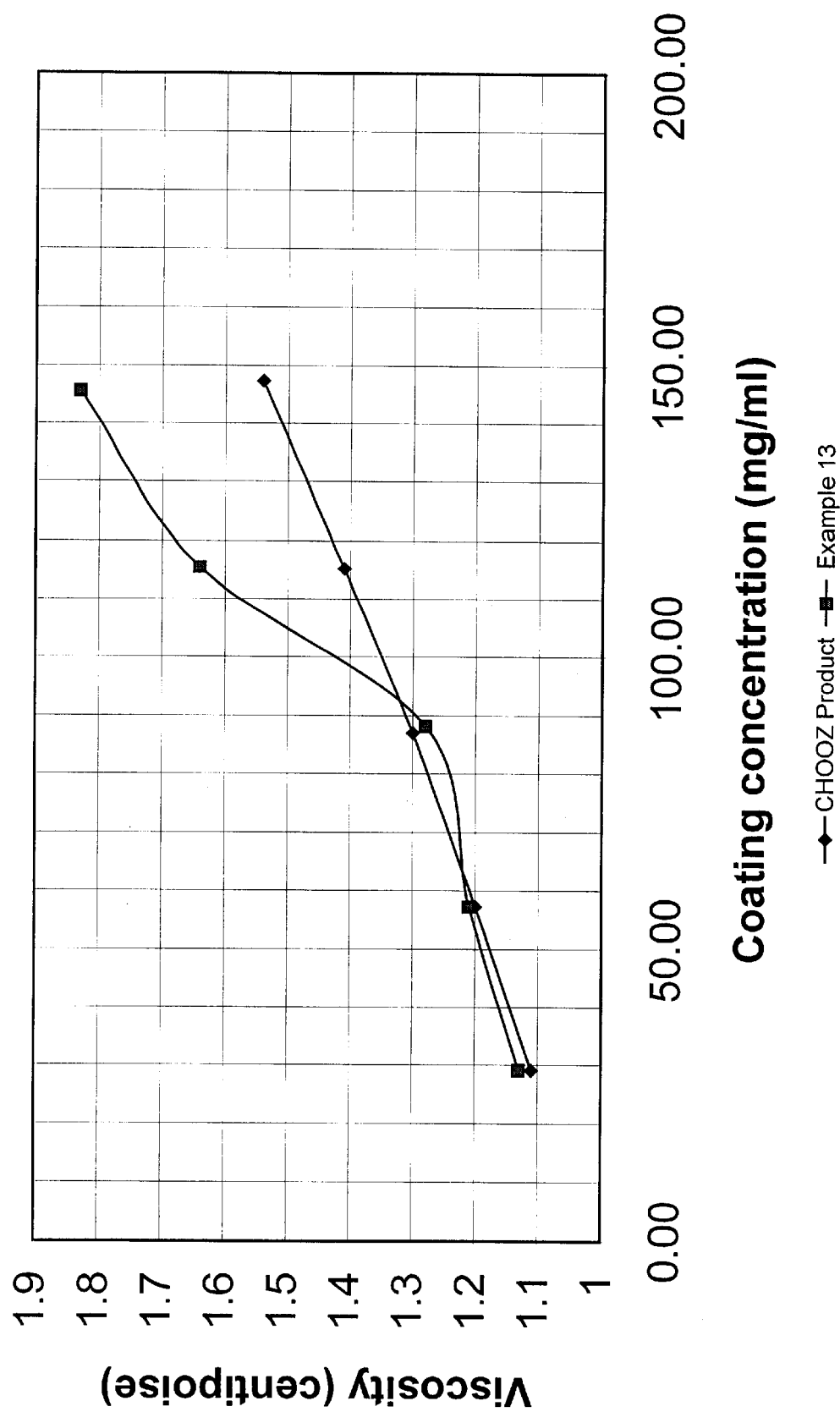
FIG. 1 is a graph showing viscosity test results for a sample product of the invention and the CHOOZ® product.

As used herein, the term "chewing gum" includes bubble gum and all other types of chewing gum. Unless specified otherwise, all percentages are weight percentages.

As mentioned above, products made by the present invention will include an antacid, such as calcium carbonate. The antacid will preferably be included as part of the coating syrup used to prepare a coated chewing gum product. A typical syrup may contain a polyol, suspended calcium carbonate, a binding agent, a high intensity sweetener and a whitener.

In a preferred embodiment of the present invention, the antacid is contained in the coating of chewing gum products, which allows a chewing gum coating to be a carrier for the antacid. Accordingly, as the chewing gum is chewed, the active antacid in the gum coating is released into the saliva and ingested to give relief from gastrointestinal disturbances in the GI tract.

The preferred antacids are generally carbonate or hydroxide salts of calcium, magnesium, aluminum, or bismuth, and are generally very water insoluble. Other antacids such as sodium bicarbonate, calcium bicarbonate, and other carbonates, silicates, and phosphates are included in this invention. When these materials are mixed with acids in the GI tract, the acids are readily neutralized to give relief from GI disturbances. Some typical consumer antacid products are: TUMS, which contains calcium carbonate; MILK of MAGNESIA, which contains magnesium hydroxide, MAALOX PLUS, which contains a combination of aluminum hydroxide and magnesium hydroxide.

For antacid chewing gum products, calcium carbonate is the most preferred antacid material. This is mostly due to the fact that the most common inert filler in chewing gum base is calcium carbonate. Calcium carbonate, along with talc, which is commonly used in bases for gum products that contain food acids to give tartness to flavors, have been used as fillers in gum base and gum products for many years.

Chewing gum bases that contain calcium carbonate do not readily release their calcium carbonate during chewing. Since calcium carbonate (or in other cases talc) is very water insoluble, it releases from gum either very slowly or over very long extended chewing. As a result, this calcium carbonate is not effective as an antacid. Generally, when calcium carbonate is added to a gum formulation separate from the gum base, calcium carbonate becomes intimately mixed with the base during chewing and also releases very slowly. However, when calcium carbonate is used in the coating of the chewing gum, it does become quickly available in the oral cavity and is ingested to be an effective antacid.

Generally, suspension coatings with calcium carbonate for an antacid gum may be made with sugar. Sugar with its naturally sweet taste masks some of the off-taste due to the use of high levels of calcium carbonate. With the advent of new coating technologies using less sweet sugarless polyols instead of sugar, the sweet taste of the coating is significantly reduced. In some coatings where xylitol is used, it is sufficiently sweet as a coating, but other polyols such as maltitol, hydrogenated isomaltulose, sorbitol, or erythritol, are not. When the coating contains high levels of calcium carbonate, the polyols generally lack sufficient sweetness to give a good tasting product. As a result, high-intensity sweeteners are preferably added to the coating containing calcium carbonate to give a high-quality, consumer-acceptable product.

For coated antacid chewing gum type products, the high level of calcium carbonate or other antacid in the coating modifies the taste quality and gum texture. The addition of high-intensity sweeteners to the gum coating improves the taste of the finished product. This also occurs in sugar coated gums as well as polyol coated gums, so aspartame or other high-intensity sweeteners may also be added to sugar coated gums with calcium carbonate or other antacids. If the high-intensity sweeter is subject to degradation, it may preferably be added as part of a different coating syrup from the coating syrup containing the calcium carbonate, as disclosed in U.S. patent application Ser. No. 09/591,256 filed Jun. 9, 2000, hereby incorporated by reference.

In general, a chewing gum composition typically comprises a water-soluble bulk portion, a water-insoluble chewable gum base portion and typically water-insoluble flavoring agents. The water-soluble portion dissipates with a portion of the flavoring agent over a period of time during chewing. The gum base portion is retained in the mouth throughout the chew.

The insoluble gum base generally comprises elastomers, resins, fats and oils, softeners and inorganic fillers. The gum base may or may not include wax. The insoluble gum base can constitute approximately 5% to about 95% by weight of the chewing gum, more commonly the gum base comprises 10% to about 50% of the gum, and in some preferred embodiments approximately 25% to about 35% by weight, of the chewing gum. In pellet gum center formulations, the level of insoluble gum base may be much higher.

In a preferred embodiment, the chewing gum base of the present invention contains about 20% to about 60% by weight synthetic elastomer, about 0% to about 30% by weight natural elastomer, about 5% to about 55% by weight elastomer plasticizer, about 4% to about 35% by weight filler, about 5% to about 35% by weight softener, and optional minor amounts (about 1% or less by weight) of miscellaneous ingredients such as colorants, antioxidants, etc.

Synthetic elastomers may include, but are not limited to, polyisobutylene with GPC weight average molecular weights of about 10,000 to about 95,000, isobutylene-isoprene copolymer (butyl elastomer), styrene-butadiene, copolymers having styrene-butadiene ratios of about 1:3 to about 3:1, polyvinyl acetate having GPC weight average molecular weights of about 2,000 to about 90,000, polyisoprene, polyethylene, vinyl acetate—vinyl laurate copolymers having vinyl laurate contents of about 5% to about 50% by weight of the copolymer, and combinations thereof.

Preferred ranges are: 50,000 to 80,000 GPC weight average molecular weight for polyisobutylene; 1:1 to 1:3 bound styrene-butadiene for styrene-butadiene; 10,000 to 65,000 GPC weight average molecular weight for polyvinyl acetate, with the higher molecular weight polyvinyl acetates typically used in bubble gum base; and a vinyl laurate content of 10–45% for vinyl acetate-vinyl laurate.

Natural elastomers may include natural rubber such as smoked or liquid latex and guayule, as well as natural gums such as jelutong, lechi caspi, perillo, sorva, massaranduba balata, massaranduba chocolate, nispero, rosindinha, chicle, gutta hang kang, and combinations thereof. The preferred synthetic elastomer and natural elastomer concentrations vary depending on whether the chewing gum in which the base is used is adhesive or conventional, bubble gum or regular gum, as discussed below. Preferred natural elastomers include jelutong, chicle, sorva and massaranduba balata.

Elastomer plasticizers may include, but are not limited to, natural rosin esters such as glycerol esters or partially hydrogenated rosin, glycerol esters of polymerized rosin, glycerol esters of partially dimerized rosin, glycerol esters of rosin, pentaerythritol esters of partially hydrogenated rosin, methyl and partially hydrogenated methyl esters of rosin, pentaerythritol esters of rosin; synthetics such as terpene resins derived from alpha-pinene, beta-pinene, and/or d-limonene; and any suitable combinations of the foregoing. The preferred elastomer plasticizers will also vary depending on the specific application, and on the type of elastomer which is used.

Fillers/texturizers may include magnesium and calcium carbonate, ground limestone, silicate types such as magnesium and aluminum silicate, clay, alumina, talc, titanium oxide, mono-, di- and tri-calcium phosphate, cellulose polymers, such as wood, and combinations thereof.

Softeners/emulsifiers may include tallow, hydrogenated tallow, hydrogenated and partially hydrogenated vegetable oils, cocoa butter, glycerol monostearate, glycerol triacetate, lecithin, mono-, di- and triglycerides, acetylated monoglycerides, fatty acids (e.g. stearic, palmitic, oleic and linoleic acids), and combinations thereof Colorants and whiteners may include FD&C-type dyes and lakes, fruit and vegetable extracts, titanium dioxide, and combinations thereof.

The base may or may not include wax. An example of a wax-free gum base is disclosed in U.S. Pat. No. 5,286,500, the disclosure of which is incorporated herein by reference.

In addition to a water-insoluble gum base portion, a typical chewing gum composition includes a water-soluble bulk portion and one or more flavoring agents. The water-soluble portion can include bulk sweeteners, high-intensity sweeteners, flavoring agents, softeners, emulsifiers, colors, acidulants, fillers, antioxidants, and other components that provide desired attributes.

Softeners are added to the chewing gum in order to optimize the chewability and mouth feel of the gum. The softeners, which are also known as plasticizers and plasticizing agents, generally constitute between approximately 0.5% to about 15% by weight of the chewing gum. The softeners may include glycerin, lecithin, and combinations thereof. Aqueous sweetener solutions such as those containing sorbitol, hydrogenated starch hydrolysates, corn syrup and combinations thereof, may also be used as softeners and binding agents in chewing gum.

Bulk sweeteners include both sugar and sugarless components. Bulk sweeteners typically constitute about 5% to about 95% by weight of the chewing gum, more typically, about 20% to about 80% by weight, and more commonly, about 30% to about 60% by weight of the gum. Sugar sweeteners generally include saccharide-containing components commonly known in the chewing gum art, including but not limited to, sucrose, dextrose, maltose, dextrin, dried invert sugar, fructose, galactose, corn syrup solids, and the like, alone or in combination. Sugarless sweeteners include, but are not limited to, sugar alcohols such as sorbitol, mannitol, xylitol, hydrogenated starch hydrolysates, maltitol, and the like, alone or in combination.

High-intensity artificial sweeteners can also be used, alone or in combination, with the above. Preferred sweeteners include, but are not limited to, sucralose, aspartame, N-substituted APM derivatives such as neotame, salts of acesulfame, alitame, saccharin and its salts, cyclamic acid and its salts, glycyrrhizin, dihydrochalcones, thaumatin, monellin, and the like, alone or in combination. In order to provide longer lasting sweetness and flavor perception, it may be desirable to encapsulate or otherwise control the release of at least a portion of the artificial sweetener. Such techniques as wet granulation, wax granulation, spray drying, spray chilling, fluid bed coating, coacervation, and fiber extrusion may be used to achieve the desired release characteristics.

Combinations of sugar and/or sugarless sweeteners may be used in chewing gum. Additionally, the softener may also provide additional sweetness such as with aqueous sugar or alditol solutions.

If a low calorie gum is desired, a low caloric bulking agent can be used. Examples of low caloric bulking agents include: polydextrose; oligofructose (Raftilose); inulin (Raftilin); fructooligosaccharides (NutraFlora); palatinose oligosaccharide; guar gum hydrolysate (BeneFiber); or indigestible dextrin (Fibersol). However, other low calorie bulking agents can be used.

A variety of flavoring agents can also be used, if desired. The flavor can be used in amounts of about 0.1 to about 15 weight percent of the gum, and preferably, about 0.2% to about 5% by weight. Flavoring agents may include essential oils, synthetic flavors or mixtures thereof including, but not limited to, oils derived from plants and fruits such as citrus oils, fruit essences, peppermint oil, spearmint oil, other mint oils, clove oil, oil of wintergreen, anise and the like. Artificial flavoring agents and components may also be used. Natural and artificial flavoring agents may be combined in any sensorially acceptable fashion.

In general, chewing gum is manufactured by sequentially adding the various chewing gum ingredients to a commercially available mixer known in the art. After the ingredients have been thoroughly mixed, the gum mass is discharged from the mixer and shaped into the desired form such as rolling sheets and cutting into sticks, extruding into chunks or casting into pellets, which are then coated or panned.

Generally, the ingredients are mixed by first melting the gum base and adding it to the running mixer. The base may also be melted in the mixer itself. Color or emulsifiers may also be added at this time. A softener such as glycerin may also be added at this time, along with syrup and a portion of the bulking agent. Further parts of the bulking agent are added to the mixer. Flavoring agents are typically added with the final portion of the bulking agent. Other optional ingredients are added to the batch in a typical fashion, well known to those of ordinary skill in the art.

The entire mixing procedure typically takes from five to fifteen minutes, but longer mixing times may sometimes be required. Those skilled in the art will recognize that many variations of the above described procedure may be followed.

After the ingredients are mixed, the gum mass is formed into pellets or balls. Pellet or ball gum is prepared as conventional chewing gum but formed into pellets that are pillow shaped, or into balls. The pellets/balls are used as cores for the coated product. The cores can be sugar or polyol coated or panned by conventional panning techniques to make a unique coated pellet gum. The weight of the coating may be about 20% to about 50% of the weight of the finished product, but may be as much as 75% of the total gum product.

Conventional panning procedures generally coat with sucrose, but recent advances in panning have allowed use of other carbohydrate materials to be used in place of sucrose. Some of these materials include, but are not limited to, sugars such as dextrose, maltose, isomaltulose and tagatose; or sugarless bulk sweeteners such as xylitol, sorbitol, lactitol, hydrogenated isomaltulose, erythritol, maltitol, and other new polyols (also referred to as alditols) or combinations thereof. The coating is preferably sugarless. These materials may be blended with panning modifiers including, but not limited to, gum arabic, gum talha, maltodextrins, corn syrup, gelatin, cellulose type materials like carboxymethyl cellulose or hydroxymethyl cellulose, starch and modified starches, vegetables gums like alginates, locust bean gum, guar gum, and gum tragacanth. Antitack agents may also be added as panning modifiers, which allow for the use of a variety of carbohydrates and sugar alcohols. Flavors may also be added with the sugarless coating to yield unique product characteristics.

As noted above, the coating may contain ingredients such as flavoring agents, as well as dispersing agents, coloring agents, film formers and binding agents. Flavoring agents contemplated by the present invention include those commonly known in the art such as essential oils, synthetic flavors or mixtures thereof, including but not limited to oils derived from plants and fruits such as citrus oils, fruit essences, peppermint oil, spearmint oil, other mint oils, clove oil, oil of wintergreen, anise and the like. The flavoring agents may be used in an amount such that the coating will contain from about 0.2% to about 3% flavoring agent, and preferably from about 0.7% to about 2.0% flavoring agent.

High-intensity sweeteners contemplated for use in the coating include but are not limited to synthetic substances, saccharin, thaumatin, alitame, saccharin salts, aspartame, N-substituted APM derivatives such as neotame, sucralose and acesulfame-K. The high-intensity sweetener may be added to the coating syrup in an amount such that the coating will contain from about 0.01% to about 2.0%, and preferably from about 0.1% to about 1.0% high-intensity sweetener. Preferably the high-intensity sweetener is not encapsulated.

Dispersing agents are often added to syrup coatings for the purpose of whitening and tack reduction. Dispersing agents contemplated by the present invention to be employed in the coating syrup include titanium dioxide, talc, or any other antistick compound. Titanium dioxide is a presently preferred dispersing agent of the present invention. The dispersing agent may be added to the coating syrup in amounts such that the coating will contain from about 0.1% to about 1.0%, and preferably from about 0.3% to about 0.6% of the agent.

When high amounts of calcium carbonate or other antacid is used, the calcium carbonate is dispersed or suspended in the coating syrup that contains the polyol, thus making a syrup suspension. Generally, as the level of calcium carbonate is increased, the bulk sweetener is decreased. Levels of calcium carbonate used may be as low as 25% of the total solids or as high as 60% of the total solids in the syrup, and more preferably will comprise about 30% to about 40% of the total solids. In preferred embodiments, the calcium carbonate will comprise about 25% to about 60% of the gum coating, and more preferably about 30% to about 40% of the gum coating. The coating will preferably contain about 30% to about 73% maltitol.

Coloring agents are preferably added directly to the syrup suspension in the dye or lake form. Coloring agents contemplated by the present invention include food quality dyes. Film formers preferably added to the syrup include methyl cellulose, gelatins, hydroxypropyl cellulose, ethyl cellulose, hydroxyethyl cellulose, carboxymethyl cellulose and the like and combinations thereof. Binding agents may be added either as an initial coating on the chewing gum center or may be added directly into the syrup. Binding agents contemplated by the present invention include gum arabic, gum talha, guar gum, karaya gum, locust bean gum, alginate gums, xanthan gum, arabinogalactan, various cellulose derivatives, vegetable gums, gelatin and mixtures thereof, with gum arabic being preferred. The binding agent is preferably used at a level of at least about 2% of the coating syrup.

The coating is initially present as a liquid syrup which contains from about 30% to about 80% of the coating ingredients previously described herein, and from about 20% to about 70% of a solvent such as water. In general, the coating process is carried out in a rotating pan. Sugar or sugarless gum center tablets to be coated are placed into the rotating pan to form a moving mass. The material or syrup suspension which will eventually form the coating is applied or distributed over the gum center tablets. Flavoring agents may be added before, during and after applying the syrup to the gum centers. Once the coating has dried to form a hard surface, additional syrup suspension additions can be made to produce a plurality of coatings or multiple layers of hard coating.

In a hard coating panning procedure, syrup is added to the gum center tablets at a temperature range of from about 100° F. (38° C.) to about 240° F. (116° C.). Preferably, the syrup temperature is from about 130° F. (54° C.) to about 200° F. (94° C.) throughout the process in order to prevent the polyol or sugar in the syrup suspension from crystallizing. The syrup suspension may be mixed with, sprayed upon, poured over, or added to the gum center tablets in any way known to those skilled in the art.

In general, a plurality of layers is obtained by applying single coats, allowing the layers to dry, and then repeating the process. The amount of solids added by each coating step depends chiefly on the concentration of the coating syrup suspension. Any number of coats may be applied to the gum center tablet. Preferably, no more than about 75–100 coats are applied to the gum center tablets. The present invention contemplates applying an amount of syrup sufficient to yield a coated comestible containing about 20% to about 75% coating.

Those skilled in the art will recognize that in order to obtain a plurality of coated layers, a plurality of premeasured aliquots of coating syrup suspension may be applied to the gum center tablets. It is contemplated, however, that the volume of aliquots of syrup suspension applied to the gum center tablets may vary throughout the coating procedure.

Once a coating is applied to the gum center tablets, the present invention contemplates drying the wet syrup suspension in an inert medium. A preferred drying medium comprises air. Preferably, forced drying air contacts the wet syrup coating in a temperature range of from about 70° F. (21° C.) to about 115° F. (46° C.). More preferably, the drying air is in the temperature range of from about 80° F. (27° C.) to about 100° F. (38° C.). The invention also contemplates that the drying air possess a relative humidity of less than about 15 percent. Preferably, the relative humidity of the drying air is less than about 8 percent.

The drying air may be passed over and admixed with the syrup coated gum centers in any way commonly known in the art. Preferably, the drying air is blown over and around or through the bed of the syrup coated gum centers at a flow rate, for large scale operations, of about 2800 cubic feet per minute. If lower quantities of material are being processed, or if smaller equipment is used, lower flow rates would be used.

The present invention also contemplates the application of powder material after applying an aliquot of coating syrup to help build up the coating.

For many years, flavors have been added to a sugar coating of pellet gum to enhance the overall flavor of gum. These flavors include spearmint flavor, peppermint flavor, wintergreen flavor, and fruit flavors. These flavors are generally preblended with the coating syrup just prior to applying it to the core or added together to the core in one or more coating applications in a revolving pan containing the cores. Generally, the coating syrup is very hot, about 130° F. (54° C.) to 200° F. (93° C.), and the flavor may volatilize if preblended with the coating syrup too early.

The coating syrup is preferably applied to the gum cores as a hot liquid, the sugar or polyol allowed to crystallize, and the coating then dried with warm, dry air. Aliquots of syrups are preferably applied in about 30 to 80 applications to obtain a hard shell coated product having an increased weight gain of about 20% to 75%. A flavor is applied with one, two, three or four or more of these coating applications. Each time flavor is added, several non-flavored coatings are applied to cover the flavor before the next flavor coat is applied. This reduces volatilization of the flavor during the coating process.

For mint flavors such spearmint, peppermint and wintergreen, some of the flavor components are volatilized, but sufficient flavor remains to give a product having a strong, high impact flavor. Fruit flavors, that may contain esters, are more easily volatilized and may be flammable and/or explosive and therefore, generally these type of fruit flavors are not used in coatings.

EXAMPLES

The following examples of the invention are provided by way of explanation and illustration.

As noted earlier, the gum formulas can be prepared as sugarless type formulations and made in a pellet or pillow shape or a round ball or any other shape of product for coating/panning. However, gum formulas for pellet centers are generally adjusted to a higher level of gum base to give a more consumer acceptable size of gum bolus.

Keeping this in mind, if a coating of about 25% of the total product is added to a pellet core as sugar or polyols, the gum base in the pellet core should also be increased by 25%. Likewise, if a 33% coating is applied, the base levels should also be increased by 33%. As a result, gum centers are usually formulated with about 25% to about 50% gum base with a corresponding decrease in the other ingredients except flavor. Even higher levels of base may be used when calcium carbonate or another antacid is added to a pellet coating. Generally flavor levels in the gum increase with the level of gum base as the base tends to bind flavors into the gum and more flavor is needed to give a good flavorful product. However flavors can also be added to the coating to give increased flavor impact and more flavor perception.

Some typical sugarless gum center formulations are shown in Table 1 that can be used as centers that are coated with calcium carbonate to give an effective antacid.

TABLE 1

| | (WEIGHT PERCENT) | | | | | | |
|---|---|---|---|---|---|---|---|
| | EX. 1 | EX. 2 | EX. 3 | EX. 4 | EX. 5 | EX. 6 | EX. 7 |
| GUM BASE | 35.0 | 35.0 | 30.0 | 35.0 | 30.0 | 40.0 | 35.8 |
| CALCIUM CARBONATE[b] | — | — | 5.0 | 15.0 | 10.0 | — | 14.5 |
| SORBITOL | 43.1 | 44.9 | 46.0 | 43.1 | 49.8 | 41.0 | 40.6 |
| MANNITOL | 10.0 | 10.0 | 5.0 | — | — | 8.0 | — |
| GLYCERIN | — | 8.0 | 2.0 | 3.0 | 8.0 | 2.0 | 3.0 |
| SORBITOL LIQUID | 10.0 | — | 10.0 | — | — | 6.0[a] | 1.05[c] |
| FLAVOR | 1.5 | 1.5 | 1.5 | 2.5 | 2.0 | 2.0 | 2.5 |
| ENCAPSULATED HIGH-INTENSITY SWEETENER | 0.4 | 0.4 | 0.5 | 1.0 | 0.2 | 0.6 | 2.0 |
| LECITHIN | — | 0.2 | | 0.4 | — | 0.4 | 0.55 |

[a]Lycasin brand hydrogenated starch hydrolyzate used instead of sorbitol liquid.
[b]This material is base filler and may not release to give an antacid effect.
[c]Water is added in place of sorbitol liquid.

In the above center formulations, the high-intensity sweetener used is aspartame, acesulfame K, or a combination. However other high-intensity sweeteners such as alitame, salts of acesulfame, cyclamate and its salts, saccharin and its salts, neotame, sucralose, thaumatin, monellin, dihydrochalcone, stevioside, glycyrrhizin and combinations thereof may be used in any of the examples with the level adjusted for sweetness.

Lycasin and other polyols such as maltitol, xylitol, erythritol, lactitol and hydrogenated isomaltulose may also be used in the gum center formulations at various levels. The texture may be adjusted by varying glycerin or sorbitol liquid.

Sweetness of the center formulation can also be adjusted by varying the level of high-intensity sweetener.

Calcium carbonate can be used in sugarless coatings with maltitol, lactitol, and hydrogenated isomaltulose. Gum arabic acts as a binding agent, film former and hardener of the coated pellet. Using a 1 gram center and maltitol in the coating, the levels of calcium carbonate in the Examples in the following table will give 250–800 mg of antacid per 1 or 2 pieces in 1.5–3.0 gram gum product pieces with a 33% to 66% coating.

TABLE 2

| | (DRY WEIGHT PERCENT) | | | | | |
|---|---|---|---|---|---|---|
| | EX. 8 | EX. 9 | EX. 10 | EX. 11 | EX. 12 | EX. 13 |
| MALTITOL | 71.5 | 54.5 | 66.8 | 51.4 | 60.8 | 50.1 |
| MALTITOL POWDER | — | — | — | 5.0 | 10.0 | 6.0 |
| GUM ARABIC | 2.0 | 4.0 | 6.0 | 2.0 | 3.0 | 6.0 |
| FLAVOR | 0.5 | 0.4 | 0.7 | 0.5 | 0.3 | 1.0 |
| TITANIUM DIOXIDE | 0.5 | 0.5 | 1.0 | 0.5 | 0.4 | 1.3 |
| TALC | 0.1 | 0.1 | 0.1 | 0.1 | 0.1 | 0.1 |
| WAX | 0.1 | 0.1 | 0.1 | 0.1 | 0.1 | 0.1 |
| CALCIUM CARBONATE* | 25.0 | 40.0 | 25.0 | 40.0 | 25.0 | 35.0 |
| ACESULFAME K | 0.3 | 0.4 | 0.3 | 0.4 | 0.3 | 0.4 |

*Calcium carbonate had a median particle size of 5.1 microns

Maltitol powder is used to dry charge in the early stages of coating. Maltitol, gum arabic and whitener are blended into the coating syrup and applied to the gum pellets.

Calcium carbonate is applied with the syrup suspension, preblended with powder maltitol or added as a dry charge. After all coating is applied and dried, talc and wax are added to give a polish.

In a similar manner, coatings with lactitol and hydrogenated isomaltulose may be made in the coating formulas in Table 2 by replacing maltitol with any one of the other polyols and maltitol powder with the polyol powder. Like maltitol, the other polyols may become sticky during the coating and drying process, so the dry powder charge may be needed to give the proper drying. In the later stages of the coating process, less gum arabic could be used and a more pure polyol syrup could be used to give a smooth surface. Also, the dry charge would only be used in the early stages of the coating process.

In addition to dry charging with the specific polyol, other ingredients may be added to the dry charge to help absorb moisture. These materials could be inert such as talc, magnesium carbonate, starches, gums like arabinogalactan, gum talha, gum arabic or other moisture absorbing materials. Also, powdered sweeteners or flavors could be added with the dry charge.

Polyols such as maltitol, lactitol and hydrogenated isomaltulose are not sufficiently sweet compared to sugar or xylitol, so high-intensity sweeteners are preferably added to the coating. Beside aspartame, other high-intensity sweeteners may also be used such as acesulfame K, salts of acesulfame, cyclamate and its salts, saccharin and its salts, alitame, sucralose, thaumatin, monellin, dihydrochalcone, glycyrrhizin, neotame, and combinations thereof. When adding calcium carbonate or other antacids, and a hot syrup is applied, heat and high pH may degrade some sweeteners, so only stable high-intensity sweeteners should be used if the high-intensity sweeter is added to the main coating syrup.

Polyols such as maltitol, hydrogenated isomaltulose, and lactitol are disaccharide polyols and will give a higher viscosity when dissolved in the same amount of water compared to sorbitol and xylitol, which are monosaccharide polyols. Thus during chewing, when the polyol dissolves and the saliva is ingested, these disaccharide polyols will be more viscous, thus allowing a longer residence time for the calcium carbonate antacid, and extending its effectiveness.

To determine if viscosity differences of the different polyols are significant, coating syrups were prepared to determine those viscosity differences. The following coating syrup formulas were made:

| | grams | | | |
|---|---|---|---|---|
| | A | B | C | D |
| Water | 153 | 153 | 153 | 153 |
| 40% Gum Talha Solution | 92 | 92 | 92 | 92 |
| Maltitol | 321.5 | — | — | — |
| Xylitol | — | 321.5 | — | — |
| Sorbitol | — | — | 321.5 | — |
| Hydrogenated Isomaltulose | — | — | — | 321.5 |
| Calcium Carbonate | 218 | 218 | 218 | 218 |
| Titanium Dioxide | 8.1 | 8.1 | 8.1 | 8.1 |
| Viscosity (centipoise)* | 190 | 106 | 128 | 185 |

*Using Brookfield DV-II, Spindle 2 at 100 rpm at 65° C.

It can be seen that the coating syrups made with disaccharides (Example A—maltitol and Example D—hydrogenated isomaltulose) had significantly higher viscosities than coating syrups made with mono-saccharides (Example B—xylitol and Example C—sorbitol).

As noted previously, pellet gum coatings dissolve quickly when the coated gum product is chewed. Antacid in the coating thus provide fast relief to the discomfort associated with excessive stomach acid. A further benefit of coated antacid gum may be due to the increase viscosity effects pellet coating ingredients may have on saliva. More viscous saliva may have a greater residence time in the esophagus and provide a greater chance of neutralizing the reflux acid associated with indigestion.

Direct viscosity measurements of saliva is difficult due to the variable nature of saliva. An in-vitro method was developed where the pellet coatings were dispersed in deionized (DI) water. The resulting fluid's viscosity was measured by the following instrument and procedures:

Use a Brookfield DV-I+ Viscometer, model LVDV-I+ version 5.0, equipped with a UL adapter. The instrument is calibrated with a Brookfield certified 4.9 centipoise calibration standard. The full scale range was 1.0 centipoise to 10.0 centipoise and was determined to be accurate to ±0.15 centipoise.

In-Vitro Method: Washed Coating Procedure

1. Weigh 4 pellets into a tare 2 oz. French Square bottle. Record the sample weight.
2. Add a 1 inch magnetic stir bar, 30 mls DI water and start a 10 minute timer.
3. Place the bottle on a magnetic stir plate and vigorously agitate for 10 minutes.
4. Remove the sample bottle and quickly decant the liquid dispersion.
5. Place the pellet centers on a paper towel and immediately measure the viscosity of the resulting liquid.
6. Briefly hand rinse the pellet centers to remove the residual liquid dispersion.
7. Remove the excess water from the centers with a paper towel and store in a desiccator for at least 16 hours.
8. Weigh the centers and calculate the removed coating weight by difference.

Normally a person would chew two pellets of gum and generate about 15 ml of saliva in 10 minutes of chewing. It is necessary to double the quantities of pellets and water in the foregoing test protocol to achieve the required volume of fluid needed for the Brookfield UL adapter.

The foregoing procedure was used to test the viscosity of dispersions made from a CHOOZ® product and a product made according to the present invention. The CHOOZ® product is distributed by Heritage Consumer Products of Brookfield, Conn. CHOOZ® is coated with sorbitol, calcium carbonate (about 50% of coating), an unknown amount (probably less than 2%) of acacia, and titanium dioxide. The inventive example used in these viscosity tests was made according to the gum center formula of Example 7 in Table 1 and coated with coating formula of Example 13 in Table 2 to yield a product containing 450 mg of calcium carbonate. Dispersion viscosity data was summarized below:

| CHOOZ ® Product | | Example 13 Product | |
|---|---|---|---|
| Coating Weight (grams) | Wash Liquid Viscosity (centipoise) | Coating Weight (grams) | Wash Liquid Viscosity (centipoise) |
| 4.62 | 1.44 | 5.47 | 1.83 |
| 4.44 | 1.38 | 5.41 | 1.84 |
| 4.26 | 1.38 | 5.47 | 1.86 |

| CHOOZ ® Product | | Example 13 Product | |
|---|---|---|---|
| Coating Weight (grams) | Wash Liquid Viscosity (centipoise) | Coating Weight (grams) | Wash Liquid Viscosity (centipoise) |
| 4.41 | 1.43 | 5.6 | 1.86 |
| 4.39 | 1.4 | 5.41 | 1.83 |
| 4.69 | 1.42 | 5.41 | 1.82 |
| Mean average | 1.41 | | 1.84 |
| Standard Deviation | 0.0256 | | 0.0167 |

A t-Test statistical comparison of the means indicated the fluid made from the coating on the Example 13 product was more viscous than the fluid made from the coating on the CHOOZ® product. However the obvious weight difference in coating may give a significant difference in viscosity, so the test procedure was modified to the following Scraped Pellet Coating Procedure:

Scraped Pellet Coating Procedure

1. Crush several pellets of gum using a mortar and pestle. Collect the fragments.
2. Further separate the cracked coating from the chewing gum center by scraping the material with a spatula or a large bore sieve screen.
3. Inspect and remove center material adhering to the coating chips with the narrow end of a laboratory spatula.
4. Weigh coating into a tare 2 oz. French Square bottle. Record the sample weight.
5. Add a 1 inch magnetic stir bar and 30 mls DI water. Cap the bottle with a Teflon lined cap.
6. Place the bottle on a magnetic stir plate and vigorously agitate until the sample is completely dissolved and dispersed.
7. Remove the sample bottle and test the liquid dispersion's viscosity at 23° C.

Results are shown in the following table and in FIG. 1.

| CHOOZ ® Product | | Example 13 Product | |
|---|---|---|---|
| Coating Weight (grams) | Viscosity (centipoise) | Coating Weight (grams) | Viscosity (centipoise) |
| 0.872 | 1.11 | 0.873 | 1.13 |
| 1.719 | 1.20 | 1.718 | 1.21 |
| 2.607 | 1.30 | 2.643 | 1.28 |
| 3.453 | 1.11 | 3.463 | 1.64 |
| 4.421 | 1.54 | 4.371 | 1.83 |

The coating dispersion viscosity difference between the CHOOZ® product and Example 13 Product is shown in FIG. 1. Note that the first 3 data points approximate the theoretical concentration equivalent to chewing about one pellet or less, for 10 minutes. The last two data points approximate chewing 1.5 to 2 pellets for 10 minutes. At the higher concentration levels, a measurable difference between coating dispersion viscosity was illustrated. Thus, the standard scrape test with a 4.5 gram quantity of coating made according to the present invention will have a viscosity of 1.6 centipoise, and preferably 1.8 centipose or higher.

As can be seen by the previous coating syrup viscosity data, most of the viscosity differences between the CHOOZ® product and the Example 13 product is probably due to the use of sorbitol in the CHOOZ® coating and the use of maltitol in the Example 13 coating. However, soluble natural gums and cellulose derivatives in a coating can also have a significant effect on viscosity. Some low viscosity gums such as gum arabic, gum talha, or arabinogalactan would have less of an affect on viscosity and would have to be used at levels higher than about 2% of the total dry solids. Other gums such as karaya gum, guar gum, locust bean gum, sodium alginate, and xanthan gum can be used at much lower levels but would contribute greatly to higher viscosity. Many of the soluble cellulose gum derivatives such as hydroxypropyl cellulose, hydroxypropyl methyl cellulose, methyl cellulose and others would also contribute to viscosity.

The preferred embodiment of the invention is made with calcium carbonate particles that give a prolonged effectiveness, preferably particles that have a median particle size of between about 3 microns and about 75 microns, and more preferably between about 3 microns and about 15 microns. This aspect of the preferred embodiment of the invention is explained more fully in a patent application entitled "Coated Chewing Gum Product Containing Antacid," Attorney Docket No. 1391/1510, filed on the same date as the present application, and hereby incorporated by reference.

It should be appreciated that the compositions and methods of the present invention are capable of being incorporated in the form of a variety of embodiments, only a few of which have been illustrated and described above. The invention may be embodied in other forms without departing from its spirit or essential characteristics. The described embodiments are to be considered in all respects only as illustrative and not restrictive, and the scope of the invention, therefore, indicated by the appended claims rather than by the foregoing description. All changes which come within the meaning and range of equivalency of the claims are to be embraced within their scope.

What is claimed is:

1. A method of making antacid coated chewing gum products comprising the steps of:
   a) providing chewing gum cores;
   b) providing a coating syrup comprising:
      i) a bulk sweetener;
      ii) calcium carbonate, wherein the calcium/carbonate comprises between about 25% and about 60% of the total solids in the coating syrup; and
      iii) a binding agent; and
   c) applying the coating syrup to the cores and drying the syrup to produce a sugarless coating on the cores;
   d) wherein the coating on the cores produces a high viscosity in saliva when the gum is chewed, in that 4.5 grams of said coating dispersed in 30 ml of water has a Brookfield viscosity at 23° C. of at least 1.6 centipoise; and
   e) wherein the calcium carbonate comprises between about 25% and about 60% of the coating.

2. The method of claim 1 wherein the bulk sweetener is a polyol.

3. The method of claim 2 wherein the polyol is a disaccharide polyol.

4. The method of claim 3 wherein the polyol is selected from the group consisting of maltitol, lactitol, hydrogenated isomaltulose and combinations thereof.

5. The method of claim 1 wherein the calcium carbonate has a median particle size of between about 3 microns and about 75 microns.

6. The method of claim 1 wherein the calcium carbonates has a median particle size of between about 3 microns and about 15 microns.

7. The method of claim 1 wherein the binding agent is selected from the group consisting of gum arabic, gum taiha, guar gum, karaya gum, locust bean gum, alginate gums, xanthan gum, arabinogalactan, cellulose derivatives, vegetable gums, gelatin and mixtures thereof.

8. The method of claim 1 wherein the calcium carbonate comprises between about 30% and about 40% of the total solids in the coating syrup.

9. The method of claim 1 wherein the calcium carbonate comprises between about 30% and about 40% of the coating.

10. The method of claim 1 wherein the coating further comprises a high-intensity sweetener.

11. The method of claiml 10 wherein the high-intensity sweetener is selected from the group consisting of sucralose, aspartame, N-substituted APM derivatives, salts of acesulfame, alitame, saccharin and its salts, cyclamic acid and its salts, glycyrrhizin, dihydrochalcones, thaumatin, monellin and mixtures thereof.

12. The method of claim 1 wherein the bulk sweetener comprises maltitol.

13. The method of claim 1 wherein the calcium carbonate is a precipitated calcium carbonate.

14. The method of claim 10 wherein the high-intensity sweetener is applied as part of a different coating syrup from the coating syrup containing calcium carbonate.

15. The method of claim 10 wherein the high-intensity sweetener comprises acesulfame K.

16. The method of claim 1 wherein a powdered bulk sweetener is applied to the cores after application of the coating syrup.

17. The method of claim 1 wherein the coating further comprises a histamine $H_2$—receptor antagonist.

18. The method of claim 17 wherein the histamine $H_2$—receptor antagonist is selected from the group consisting of cimetidine, ranitidine, famotidine, nizatidine and mixtures thereof.

19. The method of claim 17 wherein the histamine $H_2$—receptor antagonist comprises famotidine.

20. A chewing gum product made by the method of claim 1.

21. An antacid coated chewing gum product comprising:
    a) a chewing gum core; and
    b) an antacid coating on the core, the coating comprising:
        i) about 30% to about 73% maltitol;
        ii) about 25% to about 60% precipitated calcium carbonate, wherein the coating is made from a syrup and the coating syrup used to make the coating comprises calcium carbonate at a level of between about 25% and about 60% of the total solids in the syrup; and
        iii) greater than 2% of a binding agent.

22. The antacid coated chewing gum product of claim 21 wherein the binding agent is selected from the group consisting of gum arabic, gum talha, arabinogalactan and mixtures thereof.

23. The antacid coated chewing gum product of claim 21 wherein the binding agent comprises gum arabic.

24. The antacid coated chewing gum product of claim 21 wherein the coatingfurther comprises a high-intensity sweetener.

25. The antacid coated chewing gum product of claim 24 wherein the high-intensity sweetener is selected from the group consisting of sucralose, aspartame, N-substituted APM derivatives, salts of acesulfame, alitame, saccharin and its salts, cyclamic acid and its salts, glycyrrhizin, dihydrochalcones, thaumatin, monellin and mixtures thereof.

26. The antacid coated chewing gum product of claim 21 wherein the coating on the cores produces a high viscosity in saliva when the gum is chewed, in that 4.5 grams of said coating dispersed in 30 ml of water has a Brookfield viscosity at 23° C. of at least 1.6 centipoise.

27. A method of delivering an antacid to an individual that provides relief in the gastrointestinal tract comprising the steps of:
    a) providing an antacid coated chewing gum product having:
        i) a chewing gum core; and
        ii) an antacid coating on the core, the coating containing about 25% to about 60% calcium carbonate and a disaccharide polyol, the coating producing a Brookfield viscosity when 4.5 grams of coating are dispersed in 30 ml of water at 23° C. of at least 1.6 centipose, wherein the coating is made from a syrup and the coating syrup used to make the coating comprises calcium carbonate at a level of between about 25% and about 60% of the total solids in the syrup; and
    b) chewing the antacid coated chewing gum product in the mouth and swallowing the coating, the coating dispersing and dissolving to produce an increased viscosity in saliva swallowed with the coating such that the calcium carbonate has an increased residence time in the gastrointestinal tract.

* * * * *